(12) United States Patent
Enayati

(10) Patent No.: US 6,423,062 B2
(45) Date of Patent: Jul. 23, 2002

(54) BIOABSORBABLE PIN FOR EXTERNAL BONE FIXATION

(76) Inventor: Albert Enayati, 809 Carter La., Paramus, NJ (US) 07652

( * ) Notice: Subject to any disclaimer, the term of this patent is extended or adjusted under 35 U.S.C. 154(b) by 0 days.

(21) Appl. No.: 09/785,989

(22) Filed: Feb. 16, 2001

Related U.S. Application Data

(60) Provisional application No. 60/183,513, filed on Feb. 18, 2000.

(51) Int. Cl.[7] ............................................... A61B 17/56
(52) U.S. Cl. ............................ 606/59; 606/72; 606/73
(58) Field of Search ........................ 606/72, 73, 63, 606/64, 65, 29, 76, 77

(56) References Cited

U.S. PATENT DOCUMENTS

| | | | | | |
|---|---|---|---|---|---|
| 4,858,601 A | * | 8/1989 | Glisson | .................. | 606/59 |
| 4,869,242 A | * | 9/1989 | Galluzzo | .................. | 606/77 |
| 5,246,441 A | * | 9/1993 | Ross et al. | .................. | 606/77 |
| 5,470,334 A | * | 11/1995 | Ross et al. | .................. | 606/72 |
| 5,522,817 A | * | 6/1996 | Sander et al. | .................. | 606/72 |
| 5,609,595 A | * | 3/1997 | Pennig | .................. | 606/73 |
| 5,968,047 A | * | 10/1999 | Reed | .................. | 606/76 |
| 6,022,352 A | * | 2/2000 | Vandevalle | .................. | 606/73 |

* cited by examiner

*Primary Examiner*—Pedro Philogene
(74) *Attorney, Agent, or Firm*—Michael G. Petit

(57) ABSTRACT

A fixation pin adapted for use with a frame assembly for the external fixation of a bone. The fixation pin includes a metallic pin having a bioabsorbable threaded tip attached thereto. The metallic pin is a shaft having a proximal end and a shaped distal end. The bioabsorbable tip is a cylindrical unitary body having a distal end, a proximal end and a threaded outer surface therebetween. The proximal end of the tip is affixed to the shaped distal end of the metallic pin. To implant the fixation pin, a hole is drilled and tapped in a first or second bone segment comprising a fracture site. The bioabsorbable tip of the fixation pin is inserted into the hole and the fixation pin is rotated until the threaded outer surface of the tip is embedded within the bone. The proximal end of the metallic pin, projecting outwardly from the skin, is attached to a rigid frame by a clamp. Additional fixation pins are similarly implanted and attached to the frame thereby stabilizing the relative position of the first and second bone segments and accelerating healing of the fracture. After healing, the metallic pins are removed from their respective bioabsorbable tips, which remain embedded within the bone. The hybrid construction of the fixation pin minimizes trauma to both the bone and surrounding tissue during percutaneous removal of the fixation pin.

8 Claims, 4 Drawing Sheets

Prior Art

BIOABSORBABLE PIN FOR EXTERNAL BONE FIXATION

This application claims priority form Provisional application Ser. No. 60/183,513, filed Feb. 18, 2000.

BACKGROUND OF THE INVENTION

1. Field of the Invention

The invention relates generally to external bone fixation devices and more particularly to a modular fixation pin for use with an external bone fixation device.

2. Prior Art

External bone fixation devices are well known in the art of orthopedic surgery. Lichty, in U.S. Pat. No. 4,456,005, discloses an external fixation device for compressing a fracture wherein screws are anchored within the fractured bone proximally and distally to the fracture site and the screws are drawn together to promote healing. The screws are percutaneously removed following healing of the fracture. Other similar external bone fixation devices that are exemplary of the state of the art are disclosed in U.S. Pat. Nos. 4,554,915, 4,620,533, 4,919,119, 5,160,335 and 5,314,426.

External bone fixation devices are widely used in orthopedic and reconstructive surgical procedures such as the minimally invasive unification of fractured bones and distraction osteogenesis. Such external bone fixation devices, in operation, essentially include a frame having a plurality of adjustable pin attachment means thereon, and two or more bone fixation pins. The fixation pins are metallic shafts having a threaded, self-tapping invasive distal end adapted to be anchored within a bone, and a non-invasive proximal end adapted to be attached to the frame. The relative positions of the pin attachment means on the frame are adjusted to control the relative positions of the bone segments to which the respective fixation pins are anchored. When the bone segments have been manipulated and positioned as desired, the pin attachment means are immobilized until it is necessary to reposition the bone segments or to remove the fixation pins from the bone.

In accordance with the prior art, in order to implant the distal invasive end of a fixation pin within a bone, the bone is accessed by surgical means and a hole is drilled into an exposed surface of the bone. The threaded, self-tapping distal end of a metallic fixation pin is inserted into the hole, and screwed thereinto until firmly anchored. The opposing (proximal) end of the fixation pin is attached to an external frame via pin attachment means, such as a clamp, that is adjustably connected to the frame. The process is repeated for each fixation pin until the requisite fixation pins are anchored in bone and attached to the frame. The pins are explanted and frame and pins are removed once the therapeutic objective has been achieved.

As will be readily appreciated by those skilled in the art, the self-tapping threads, machined on the distal end of bone fixation pins in accordance with the prior art, are sharp in order to avoid cracking the bone during insertion of the pin thereinto. After the invasive end of such prior art fixation pins are implanted within a bone, the surrounding, sometimes inflamed, soft tissue closes in around the shaft of the pin and is in intimate contact therewith. When the fixation pin is percutaneously explanted, counterclockwise rotation of the pin is required in order to back the pin out of the hole. During pin removal, the sharp, metallic, self-tapping threads on the pin may cause damage to delicate surrounding tissue structures such as vascular and nerve tissue. There remains a need for a bone fixation pin which minimizes damage to tissue when removed from a bone.

SUMMARY OF THE INVENTION

It is a first object of the invention to provide a fixation pin for use with an external bone fixation device wherein when the fixation pin is percutaneously removed from a bone, the damage to tissue adjacent the fixation pin is minimized.

It is a second object of the invention to provide a bone fixation pin meeting the first objective which can be used with a variety of currently available bone fixation frames for performing a variety of procedures requiring the use of a bone fixation device.

It is yet another object of the invention to provide a hybrid bone fixation pin meeting the above objectives, at least a portion of which is biodegradable.

The features of the invention believed to be novel are set forth with particularity in the appended claims. However, the invention itself, both as to organization and method of operation, together with further objects and advantages thereof may be best understood by reference to the following description taken in conjunction with the accompanying drawings in which:

DESCRIPTION OF THE PREFERRED EMBODIMENTS

Figure 1:
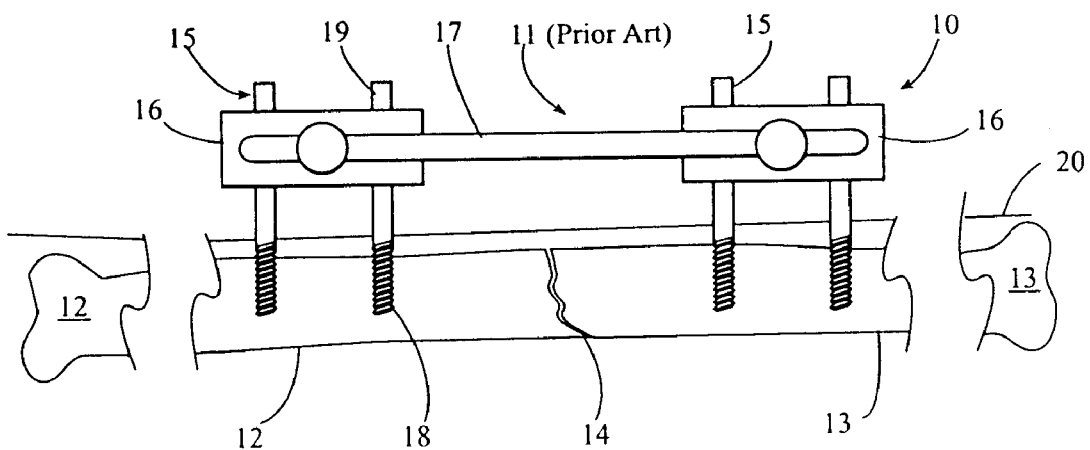
FIG. 1 is a schematic view showing an external bone fixation device comprising a prior art frame and four modular bone fixation pins of the present invention attached to a fractured bone.

Turning first to FIG. 1, an external bone fixation device 10 is shown in schematic view, illustrating the attachment of a prior art frame 11 to the bone segments 12 and 13 comprising a fracture 14 in a bone. Bone fixation pins 15 are attached to the frame 11 by means of bone attachment clamps 16 which are slidably mounted on a rod 17. In accordance with the present invention, the bone fixation pins 15 have an invasive bioabsorbable tip 18 anchored within one of the bone segments 12 or 13, and a metallic pin 19 having a distal end 31 (FIG. 3) affixed to the bioabsorbable tip and a proximal end 21 (FIG. 2) projecting upwardly through the skin 20 to provide a mechanical connection between the bone segments 12 and 13 and the frame 11.

Figure 2:
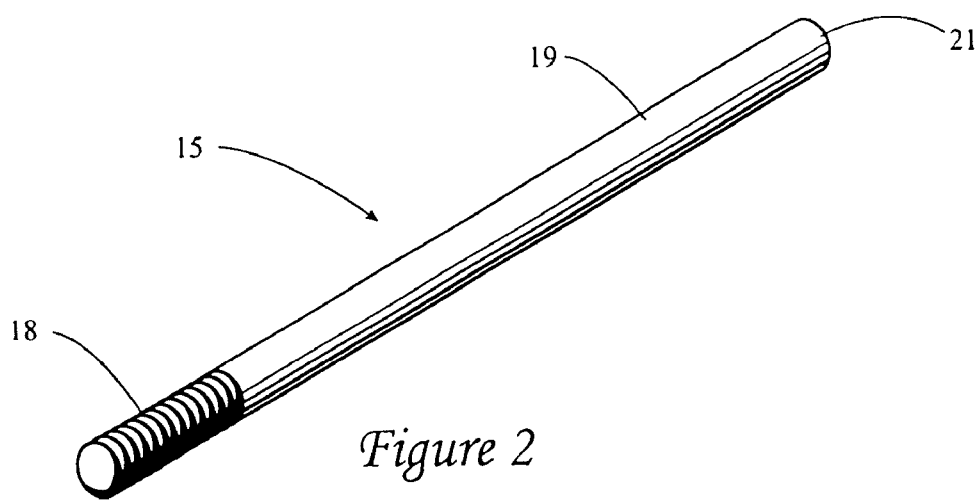
FIG. 2 is a perspective view of a modular bone fixation pin in accordance with the present invention.
Figure 3:
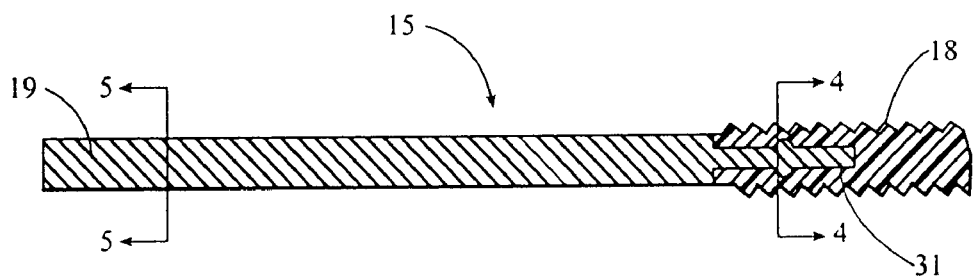
FIG. 3 is a longitudinal cross-sectional view of the modular bone fixation pin of FIG. 2.
Figure 4:
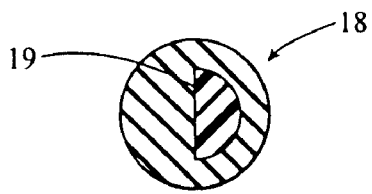
FIG. 4 is a transverse cross-sectional view of a preferred embodiment of the bioabsorbable tip portion of the bone fixation pin of FIG. 3, taken along section line 4—4 of FIG. 3.
Figure 5:
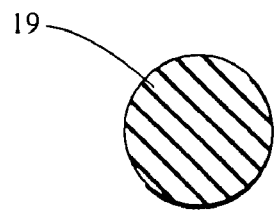
FIG. 5 is a transverse cross-sectional view of the metallic pin portion of the bone fixation pin of FIG. 3, taken along section line 5—5 of FIG. 3.

A fixation pin 15 in accordance with the present invention is shown in perspective view in FIG. 2 and horizontal cross-sectional view in FIG. 3. The fixation pin 15 is modular in construction, comprising a bioabsorbable tip portion 18 affixed to a metallic pin portion 19. The bioabsorbable tip portion 18, hereinafter alternatively referred to as "the bioabsorbable tip", is of unitary construction and fabricated from a bioabsorbable material. The bioabsorbable tip 18 overlies the distal end 31 of the metallic pin portion 19 (hereinafter referred to in the alternative as "the metallic pin", and has a threaded outer surface. The metallic pin 19 is preferably of unitary construction and has a proximal end 21 and a distal end 31 (FIG. 3) which is embedded within the bioabsorbable tip 18. The metallic pin is fabricated from a surgically acceptable metal such as stainless steel, titanium or cobalt-chrome alloy which has a high shear and axial loading strength and is not bioabsorbable. Selected cross-sectional views of the fixation pin 15 along section lines 4—4 and 5—5 of FIG. 3 are shown in FIGS. 4 and 5 respectively.

Figure 6:
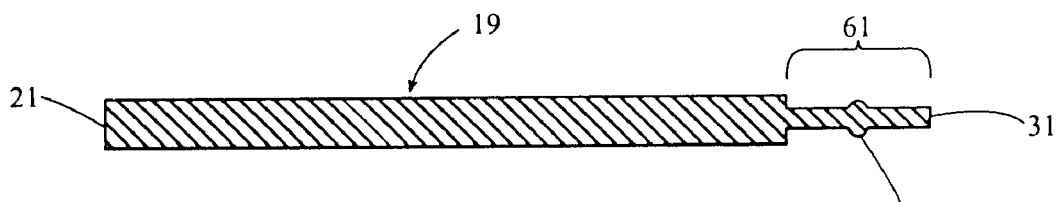
FIG. 6 is a longitudinal cross-sectional view of an embodiment of the metallic pin portion of a bone fixation pin illustrating a shaped distal end portion which is enveloped by the bioabsorbable tip in the bone fixation pin.
Figure 7:
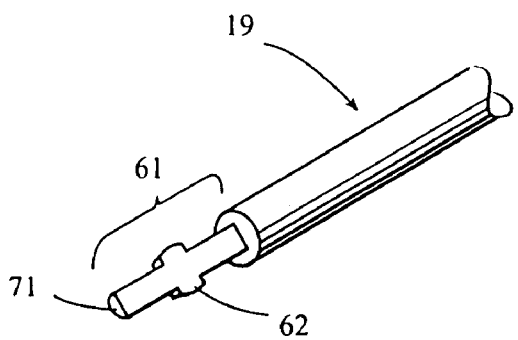
FIG. 7 is an end perspective view of an embodiment of the metallic pin portion of a bone fixation pin in accordance with FIG. 6, illustrating a shaped distal end having a generally semicircular cross-section.
Figure 8:
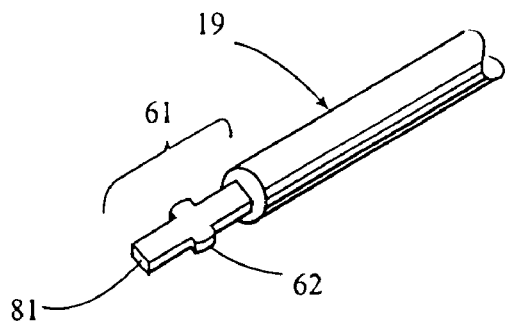
FIG. 8 is a perspective end view of a second embodiment of a metallic pin portion of a bone fixation pin in accordance with the present invention, illustrating a shaped distal end having a generally square or rectangular cross-section.
Figure 9:
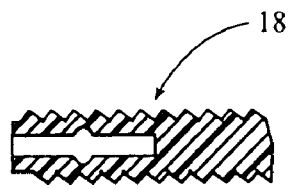
FIG. 9 is a longitudinal cross-sectional view of a bioabsorbable tip of the bone fixation pin of FIG. 3, with the shaped distal end of the metallic pin removed.

A cross-sectional view of a metallic pin in accordance with a preferred embodiment of the invention is shown at numeral 19 in FIG. 6. The metallic pin 19 has a proximal end 21 and a distal end 31. A shaped portion 61 of the length of the pin 19 adjacent the distal end 31 is constricted and shaped for entangling engagement with the bioabsorbable tip portion 18 of the fixation pin 15 when the bone fixation pin 15 is rotated during threaded engagement with the bone. FIGS. 7 and 8 illustrate, in perspective view, a shaped portion 61 having a semicircular cross-sectional shape 71, and a square or rectangular cross-sectional shape 81 respectively. The shaped portion 61 of the metallic pin 19 preferably includes an expanded portion or shoulder 62 as shown in FIGS. 6–8. The shoulder 62 provides additional means for entangling engagement between the shaped portion 61 of the metallic pin 19 and the bioabsorbable tip 18 when an axially directed separating force is applied to the fixation pin.

The term "bioabsorbable material", as used herein, means that at least a portion of the subject material is degraded or absorbed by the body between the time of implantation of the material within the body and the time of explantation therefrom. Examples of suitable bioabsorbable materials which may be employed in the fabrication of the bioabsorbable tip 18 of the fixation pin 15 include polymers or copolymers of lactide, glycolide, caprolactone, polydioxanone, trimethylene carbonate, polyorthoesters and polyethylene oxide. The choice of bioabsorbable material used will generally depend upon the particular application. A copolymer which is enjoying wide use in bone fixation applications, particularly bone screws, is 70:30 Poly(L-Lactide-Co-D,L-Lactide), marketed under the trade name RESOMER LR708, by Boehringer Inglheim.

The fixation pin 15 in accordance with the present invention may be made by insertion molding. Polymeric bioabsorbable materials may be formed into various shapes by injecting a softened mass or a high temperature melt of the polymer into a heated mold. In the process of insertion molding, the shaped portion 61 of a metallic pin 19 is inserted into a high temperature mold and the softened polymeric mass or viscous melt is injected into the mold to envelop the shaped portion 61 of the metallic pin and conform to a threaded surface of the mold. The molded polymer mass or melt is cooled, with or without annealing, and the fixation pin released from the mold. The shoulder 62 on the shaped portion 61 of the metallic pin 19 prevents the bioabsorbable tip 18 from being removed from the metallic pin when tension is applied therebetween by providing an entanglement therebetween.

Those skilled in the art will recognize the disadvantages inherent in melting a polymer prior to molding such as the loss of tensile strength which accompanies the disorganization of polymer chain alignment which defines a melt. Shalaby et al., in U.S. Pat. No. 5,529,736, discuss means for improving tensile strength of molded bioabsorbable polymers. More particularly, the inventors' disclose a mold and method for increasing the rotational alignment of polymer chains when the polymer is heated to a temperature near its melting point. The process, referred to as orthogonal unidirectional orientation, employs the high pressure-high temperature extrusion of a polymer melt through a heated die.

Figure 10:
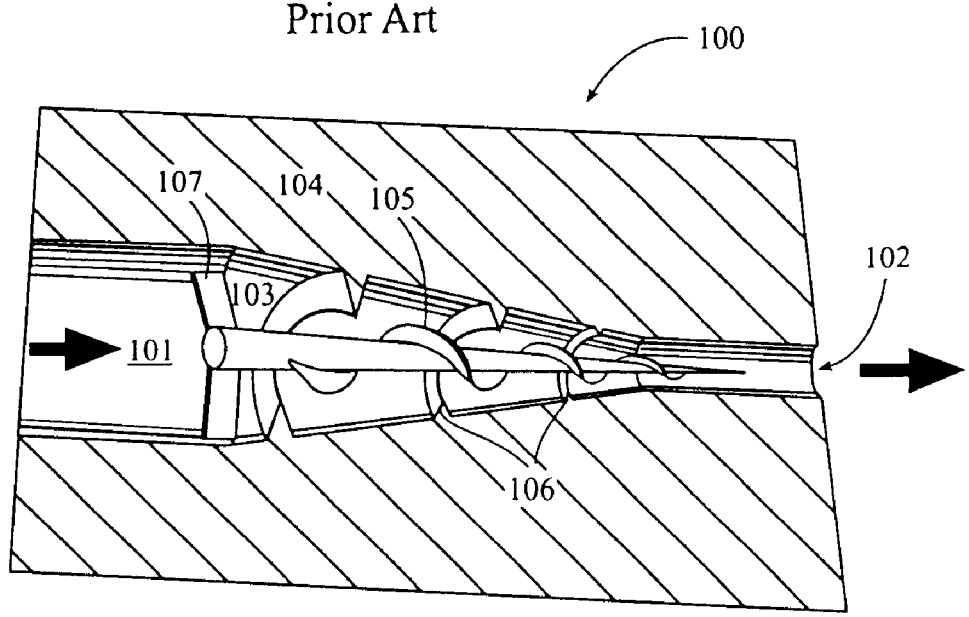
FIG. 10 is a somewhat perspective cross-sectional view of a mold injector nozzle in accordance with the prior art, which may be used for rotationally orienting polymer chains prior to injecting a fluidic polymer mass such as a biodegradable polymer, under pressure, into the bioabsorbable tip mold shown in FIG. 11.
Figure 11:
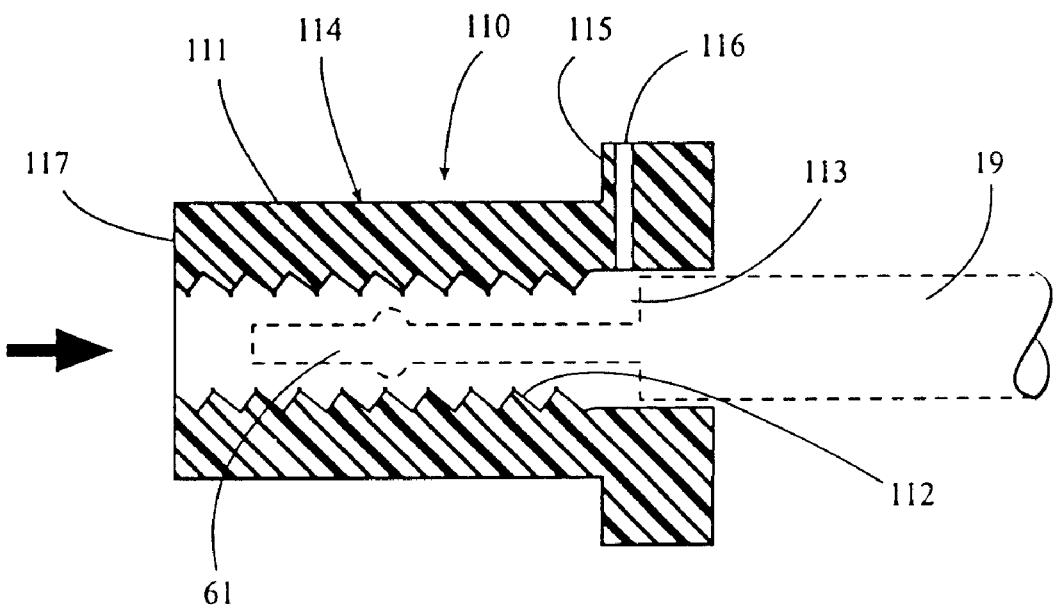
FIG. 11 is a cross-sectional side view of a mold that may be used for both forming the bioabsorbable tip and attaching the tip to the shaped distal end of the metallic pin portion of a bone fixation pin in accordance with the present invention.

With reference to FIG. 10, a prior art heated mold, shown in somewhat perspective cross-sectional view in accordance with '736, is adapted to provide a heated injection nozzle 100 for a heated mold such as the mold shown at 110 in FIG. 11 used to fabricate a fixation pin in accordance with the present invention. The injection nozzle 100 comprises a cylindrical intake port 101, a cylindrical outlet aperture 102 and a conical, funnel-shaped cavity 103 having a mandrel 104 axially disposed therewithin. The mandrel 104 has a threaded outer surface 105. The inner surface of the funnel-shaped cavity 103 has a thread 106 which cooperates with the mandrel to rotate a polymeric extrudable mass (not shown) transported in the direction, indicated by the heavy arrows, of the outlet aperture 102.

The die outlet aperture 102 may be modified to receive a mold 110 having a tip cavity 111 as shown in FIG. 11. The interior cavity 111 has a threaded inner surface 112 and an insertion aperture 113 through which the shaped portion 61 of a metallic pin 91 may be inserted into the cavity 111. The outer surface 114 of the mold 110 is dimensioned to fit within the outlet aperture 102 of the injection nozzle 100. The outer surface 114 of the tip mold 110 may be threaded to matingly engage a thread tapped within the cylindrical tube comprising the outlet aperture 102 of injection nozzle 100. The tip mold 110 has a flange 115 with a cavity pressure relief duct 116 therewithin. In use, the distal end 117 of the tip mold 110 is inserted into the outlet aperture 102 of the injection nozzle and advanced thereinto until the trailing flange 115 is in sealing engagement with the surface of the injection nozzle adjacent the outlet aperture. With the injection nozzle and the tip mold at or near the melting point of a bioabsorbable polymer, and the shaped portion 61 of the metallic pin 19 disposed within the mold cavity 111, as shown in dotted outline in FIG. 11, the polymer is forced through the injection nozzle under pressure. The mold is cooled, opened, and the fixation pin removed.

Figure 13:
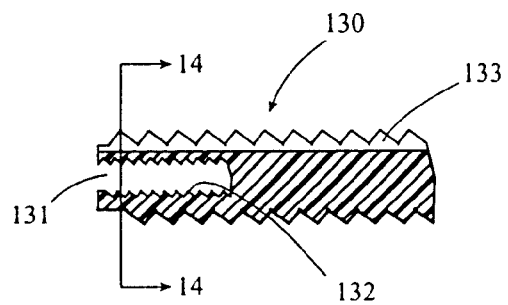
FIG. 13 is a side cross-sectional view of a bioabsorbable tip adapted for releasable attachment to the distal end of the metallic pin of FIG. 12.
Figure 14:
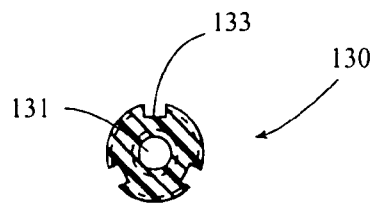
FIG. 14 is an end view of the bioabsorbable tip of FIG. 13 taken along section line 14—14 showing an indentation on the outer surface of the bioabsorbable tip which comprises a longitudinal groove.

It may be desirable to use a bioabsorbable material for making the bioabsorbable tip that does not undergo appreciable biodegradation during the healing period. In such a case, it is advantageous to provide a bone fixation pin that meets the aforesaid objectives of the present invention and wherein the bioabsorbable tip remains embedded within the bone when the metallic pin is removed. A particularly preferred embodiment of a metallic pin and bioabsorbable tip comprising a bone fixation pin in accordance with the particularly preferred embodiment of the present invention is illustrated in FIGS. 12–14.

Figure 12:
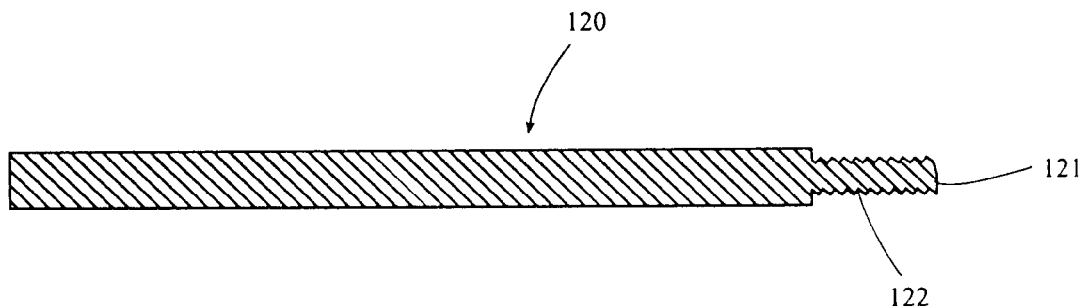
FIG. 12 is a longitudinal cross-sectional view of a metallic pin which, together with the bioabsorbable tip of FIG. 13, comprises a particularly preferred embodiment of a bone fixation pin in accordance with the present invention.

With reference now to FIG. 12, the particularly preferred embodiment of the metallic pin 120 has a distal end 121 having a cylindrical cross-section and a right handed thread 122 on the outer surface thereof. A bioabsorbable tip adapted for releasable attachment to the threaded outer surface 122 on the distal end 31 of the metallic pin 120 is indicated at 130 in FIG. 13. The bioabsorbable tip 130, illustrated in londitudinal cross-section in FIG. 13, includes an axial cavity 131 with a cylindrical threaded surface 132 that receives and matingly engages the threaded outer surface 122 of the metallic pin 120. The bioabsorbable tip 130 preferably includes at least one indentation 133 on the outer surface thereof such as, for example, the groove shown at 133 in FIG. 13. The purpose of the indentation is to permit osseous ingrowth thereinto during the healing process. Such ingrowth prevents the bioabsorbable tip 130 from being unscrewed from the threaded hole drilled in the bone.

In operation, a practitioner screws the bioabsorbable tip 130 onto the distal end 121 of the metallic pin 120 to assemble the bone fixation pin. A hole is drilled in a bone adjacent a fracture site and the bioabsorbable tip 130 portion of the bone fixation pin screwed thereinto. The process is repeated until the requisite pins are implanted in the bone and a frame is attached to the fixation pins. When healing of the fracture is complete, the metallic pins 120 are unscrewed from the respective bioabsorbable tips 130 and removed. Since the threaded outer surface on the distal end 121 of the metallic pin 120 presents a smaller cross-section than the portion of the metallic pin proximal thereto, the threads do not damage soft tissue adjacent to the pin during pin removal. The bioabsorbable tip 130 remains within the bone to be slowly absorbed by the body.

After healing of the fracture, the metallic pins are removed and their respective bioabsorbable tips remain embedded within the bone. It is customary that a bioabsorbable or non-bioabsorbable cap or plug be inserted into the bioabsorbable tip remaining in the bone to fill the gap formed therein by the removal of the metallic pin. The metallic pins having a bioabsorbable tips may be used with both internal and external fixators. The construction of the metallic pins disclosed herein may be used to advantage with other metallic fasteners such as, screws, pins, rivet system or any other fasteners capable of securing internal bone plates or external fixators to the bone for healing a bone fracture.

While particular embodiments of the present invention have been illustrated and described, it would be obvious to those skilled in the art that various other changes and modifications can be made without departing from the spirit and scope of the invention. For example, the bioabsorbable tip 130 may have a female left handed thread within the axial cavity 131 that matingly engages a male left handed thread on the outer surface of the distal end of the metallic pin. The outer surface of the bioabsorbable tip 130 may have a male right handed thread thereon that engages the bone when it is screwed into a hole drilled thereinto. It is therefore intended to cover in the appended claims all such changes and modifications that are within the scope of this invention.

What is claimed is:

1. A bone fixation pin for insertion into a hole drilled in a bone, thereafter a portion of said bone fixation pin being operable for attachment to an external bone fixation device, comprising: (a) a metallic pin having a proximal end adapted for attachment to an external bone fixation device, and a shaped distal end and a length therebetween; and (b) a bioabsorbable tip having a proximal end affixed to said shaped distal end of said metallic pin, and a distal end and a threaded outer surface therebetween, wherein said shaped distal end of said metallic pin lockingly engages said proximal end of said bioabsorbable tip to prevent separation of said metallic pin and said bioabsorbable tip.

2. The bone fixation pin of claim 1 wherein said metallic pin is of unitary construction and made from a material selected from the group comprising stainless steel, titanium and cobalt-chrome alloy.

3. The bone fixation pin of claim 1 wherein said bioabsorbable tip is of unitary construction and made from a bioabsorbable material selected from the group consisting of polymers or copolymers of lactide, glycolide, caprolactone, polydioxanone, trimethylene carbonate, polyorthoesters and polyethylene oxide.

4. The bone fixation pin of claim 2 wherein said bioabsorbable tip is of unitary construction and made from a bioabsorbable material selected from the group consisting of polymers or copolymers of lactide, glycolide, caprolactone, polydioxanone, trimethylene carbonate, polyorthoesters and polyethylene oxide.

5. The bone fixation pin of claim 1 wherein said shaped distal end of said metallic pin lockingly engages said bioabsorbable tip to prevent separation of said bioabsorbable tip from said metallic pin when subjected to mechanical force.

6. The bone fixation pin of claim 1 wherein said proximal end of said metallic pin is adapted to lockingly engage a clamp on a frame of a bone fixation device.

7. The bone fixation pin of claim 6 wherein said bioabsorbable tip has a threaded cylindrical outer surface.

8. The bone fixation pin of claim 7 wherein said threaded cylindrical outer surface further incudes a groove therein, said groove having a direction that is substantially orthogonal to threads comprising said threaded outer surface.

* * * * *